(12) United States Patent
Zamfes (10) Patent No.: US 6,290,000 B1
(45) Date of Patent: Sep. 18, 2001

(54) QUANTIFICATION OF THE CHARACTERISTICS OF POROUS FORMATIONS WHILE DRILLING

(76) Inventor: Konstandinos S. Zamfes, 1830-10$^{th}$ Avenue, S.W., Calgary, Alberta (CA), T3C 0J8

( * ) Notice: Subject to any disclaimer, the term of this patent is extended or adjusted under 35 U.S.C. 154(b) by 0 days.

(21) Appl. No.: 09/461,019

(22) Filed: Dec. 15, 1999

(30) Foreign Application Priority Data

Dec. 16, 1998 (CA) .................................................. 2256248

(51) Int. Cl.$^7$ .................................................. E21B 49/08
(52) U.S. Cl. .................................................. 175/50; 73/153
(58) Field of Search .................................................. 175/50, 42, 48; 73/153, 155, 151

(56) References Cited

U.S. PATENT DOCUMENTS

| | | | |
|---|---|---|---|
| 4,765,182 | * 8/1988 | Boone | 73/153 |
| 4,833,915 | * 5/1989 | Radd et al. | 73/153 |
| 5,084,617 | * 1/1992 | Gergely | 250/253 |
| 5,277,263 | * 1/1994 | Amen | 175/42 |
| 5,936,405 | * 8/1999 | Prammer et al. | 324/303 |

* cited by examiner

Primary Examiner—Robert E. Pezzuto
(74) Attorney, Agent, or Firm—Sean W. Goodwin (57) ABSTRACT

A method is provided for establishing the quantity and quality of hydrocarbons in the pores of a formation while drilling. One sensor (TG), applied to gas liberated from drilling mud, outputs a signal proportional to the concentration of hydrocarbons. Additional information acquired while drilling is combined with the TG analysis for quantifying a fraction of hydrocarbon in the pores of the drilled formation. Further and better quantification of hydrocarbons is achieved by normalizing drilling characteristics which are independent of porosity such as mud weight, weight on bit, bit rotational speed, and sampling dilution compared to the overall circulation of mud. Further, quality of the hydrocarbons is determinable using a second gas sensor which outputs a decreasing signal with increased concentrations of heavy hydrocarbons in the liberated gas and outputs an increasing signal with increasing concentrations of light hydrocarbons. The ratio of the first TG signal to the difference of the first and second signals (DTG) is indicative of the quality of the hydrocarbon.

11 Claims, 9 Drawing Sheets

QUANTIFICATION OF THE CHARACTERISTICS OF POROUS FORMATIONS WHILE DRILLING

FIELD OF THE INVENTION

This invention relates to methods of determining the hydrocarbon content and quality of fluid in pore spaces of a formation while drilling therethrough.

BACKGROUND OF THE INVENTION

Ideally, while drilling a well into formations which may or may not contain commercially exploitable hydrocarbon deposits, one would like to identify whether:

the formation being drilled is porous, and thus a candidate for bearing hydrocarbons and capable of economical production rates;

the fluid contained within the porous formation are hydrocarbons; and the hydrocarbons in the pores are light (C1—methane or C2—Ethane and of less interest) or are heavier (C3—Propane, C4—Butane and C5—Pentanes—the heavier hydrocarbons and thus of commercial interest).

Whether a formation is permeable or not is a function of whether the pores are connected. The relationship between porosity and Permeability is not reviewed in detail here.

Generally, when drilling an oil well, there is a rig drilling a wellbore down through a variety of 'dry' and hydrocarbon-bearing formations. Drilling fluid or mud is pumped downhole through the drill string to the bit to flush any hydrocarbons and solids from around the bit. The mud flows up the annulus between the wellbore and the drilling string, to the surface for removal of solids and cuttings in an active mud system.

Mud carries back cuttings and solids and fluids associated with the formation currently being drilled. At the active mud system, a study of the solids and gases in the mud can be performed for determining an indication of the properties of the formations being penetrated. The mud can be analysed for grain distribution and rock type, and the gases carried with the mud can be analysed for hydrocarbon content.

The drilling rig typically provides additional information regarding the formation such as the drill string rpm (RPM), force on the bit (FOB), rate of penetration (ROP) and mud weight (MW) all of which suggest characteristics of the formation. Additional factors include the mud viscosity (MV) and mud filtrate (MF).

After drilling, gamma ray, electrical resistivity, and neutron testing tools are typically taken by running one or more tools downhole to the formation of interest. These tests are often referred to collectively as E-logs.

E-logs themselves can be indicative of the lithology (type of rock) and its relative porosity (Shale being low in porosity and sandstone being higher). Gamma Ray tools work through steel casing and measure natural radiation in formations. Gamma Rays tools can differentiate between shale and sand (shale being more radioactive than sand). Electrical resistivity tools to differentiate between the lower conductivity of hydrocarbon bearing and higher conductivity water-bearing formations. Neutron tools emit gamma rays to detect variations in the element of hydrogen in the formation.

The E-logs can be correlated with the mud analyses (such as hydrocarbon gas detection) to determine whether or not a formation which was traversed should be of interest or not.

Taken individually, mud gas analysis, drilling parameters and E-Logs may be insufficient to categorically state that the wellbore has been drilled into or has passed a zone of interest. In combination however, the independent factors are usually enlightening and interest on non-interest can be stated with some confidence.

Ideally however, identification of formations of interest would be obtained WHILE drilling. This needs to be accomplished by taking overall real-time measurements while drilling oil wells. Factors which need to be ascertained are, whether a formation is porous, whether fluids within any pores are hydrocarbon and if so, are they light or heavy hydrocarbons.

E-logs can be used to determine whether a formation is porous, unfortunately only obtained after drilling or with a costly and significant interruption. Additionally, while drilling, a geologist's report provides qualitative analysis only. Some drilling parameters indicate more porous rock such as experiencing a fast ROP, a lower FOB and higher achievable RPM.

Techniques for determining whether hydrocarbon in the pore is gas or oil include neutron tool E-logs, as described above, but are only available after the fact. While drilling however, gas can liberated from a slip stream of mud returning from the wellbore by separation of the gas from mud in a gas trap. The gas is analysed using real-time sensors. One sensor is a Total Gas sensor (TG) which measures any instance of hydrocarbons (substantially Methane (C1) through pentane (C5)—measured in ppm on a methane scale). TG is used as an indication whether any hydrocarbons are present at a certain depth. TG is unable to differentiate between light and heavy hydrocarbons however.

Accordingly, there is a demonstrated need in the industry for new techniques for determining whether a zone is of interest, before significantly overdrilling or missing a zone entirely.

SUMMARY OF THE INVENTION

A novel method is provided for establishing both the quality of the hydrocarbon in a formation while drilling and the fraction of the pore which contains hydrocarbon.

The output of one sensor, normalized for the drilling rate, volumes drilled and mud flow rates enables one to determine the fraction of the formation's pores which contain hydrocarbons.

By comparing two sensors of differing responses, the quality of the hydrocarbons is determinable.

In a broad aspect then, the fraction of hydrocarbons in the pores of a fluid-containing formation is determined while drilling comprising the steps of:

analysing the mud returning up the wellbore using a TG sensor for establishing TG values which increase with increasing concentrations of hydrocarbons;

determining a dilution factor for the volume of mud being analysed by the TG sensor compared to the overall circulation of mud;

determining a porosity factor for the drilled formation, preferably by normalizing the rate of BIT penetration by a reciprocal of the unit wellbore volume drilled; and normalizing the TG by the dilution factor over the porosity factor for establishing hydrocarbon saturation index values indicative of the fraction of the pore space which is hydrocarbon.

In another aspect, a method is provided for determining the characteristics of the hydrocarbon fluid comprising the steps of:

analysing the mud returning up the wellbore using the TG sensor, analysing the mud returning up the wellbore using a DTG sensor for establishing DTG values which increase with increasing concentrations of light hydrocarbons and which decrease with increasing concentrations of heavier hydrocarbons; and determining the ratio of TG values over DTG values for establishing hydrocarbon ratio values indicative of the quality of the hydrocarbons.

BRIEF DESCRIPTION OF THE DRAWINGS

FIG. 5b is the first part of an E-log corresponding to and according to FIG. 5a.

FIG. 7b is the first part of an E-log corresponding to and according to FIG. 7a.

DETAILED DESCRIPTION OF THE PREFERRED EMBODIMENT

The present invention combines a plurality of while drilling analyses for establishing measures or indications of the porosity of a formation and the nature of its fluid content. Applicant uses both conventional Total Gas (TG) and novel Differential Total Gas (DTG) sensors to analyse gas liberated from drilling muds. The DTG sensor is disclosed in greater detail in co-pending U.S. patent application Ser. No. 09/301,726, filed Apr. 29, 1999 by applicant and which is incorporated in its entirety herein. To aid in the readability of the disclosure, portions of this disclosure are reproduced herein.

Figure 1:
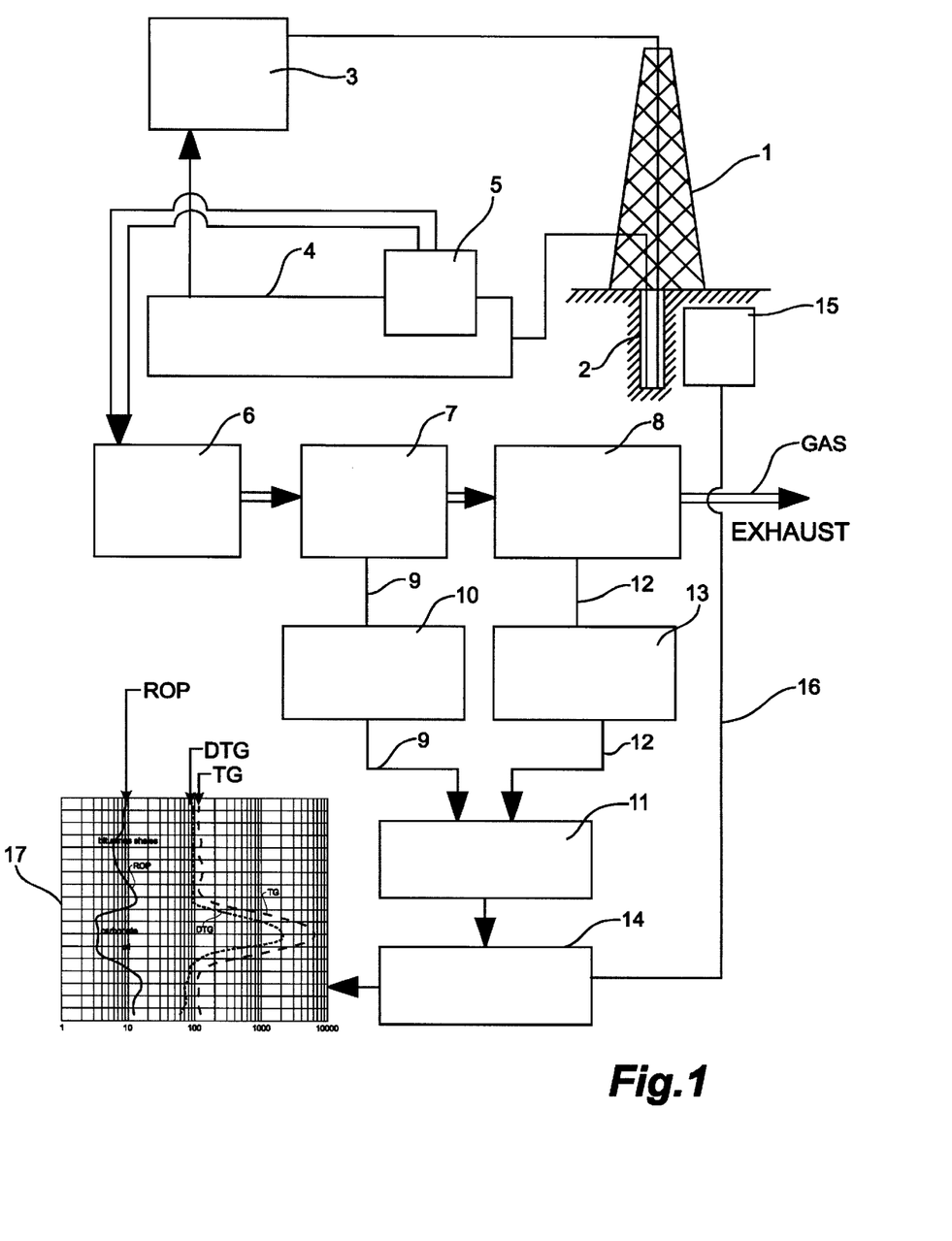
FIG. 1 is a flow chart of a drilling mud flow system, a gas sampling, a gas detection and a TG and DTG sensor signal output on a strip chart.

Generally, and having reference to FIG. 1, a drilling rig 1 drills a well 2 into a formation. Mud M is used to aid in drilling and conveying cuttings from the well 2 to the surface. Mud M is delivered in a closed loop system comprising a mud pump 3 which circulates mud M to the well 2, out of the well, to a mud tank 4 for separating cuttings and other solids from returning mud M, and back to the mud pump 3. A sample of the cuttings is used for extracting certain analyses described later, such as for determining and environmental index.

A gas trap 5 separates or extracts gas (GAS) from the mud M. The extracted gas passes through sample drier 6 to produce a dry gas sample.

The gas sample GAS is directed through a first gas sensor 7 and through second gas sensor 8. The gas sample GAS is then exhausted to atmosphere (subject to environmental constraints, e.g. if the gas not sour).

The first gas sensor 7 is a total-gas (TG) sensor and is sensitive to variable relative concentrations of predominately methane ($CH_4$) in the gas sample. The TG sensor responds to all hydrocarbons regardless of the weight of the hydrocarbon, producing an output signal as if the sampled gas was equivalent to methane.

The second gas sensor 8 is sensitive to variable relative concentrations of heavier hydrocarbons such as ethane ($C_2H_6$) through pentane ($C_5H_{12}$) in the dried gas GAS. Preferably, when exposed to light hydrocarbons, the second sensor 8 behaves similarly to the first sensor, however, when exposed to heavy hydrocarbons, it behaves in an opposite manner as described in greater detail below.

Figure 2:
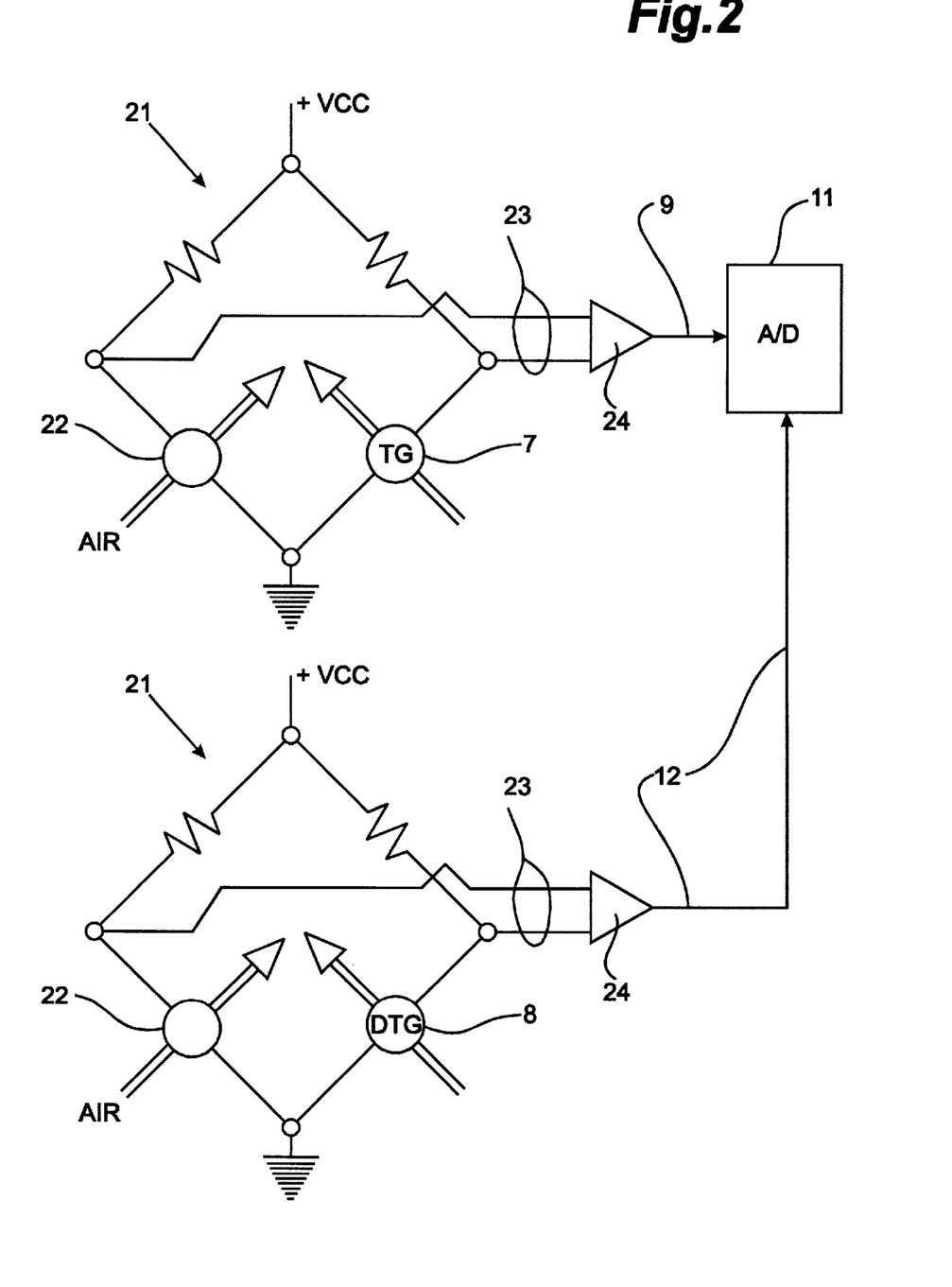
FIG. 2 is a typical circuit for conditioning the signal from the gas sensors.

The first and second sensors 7,8 are electrically positioned in a Wheatstone bridge 21 (FIG. 2) for applying a voltage across the sensor. Sufficient voltage is applied to heat the sensor. When gases are conducted through the sensors which they are sensitive to, the sensor's resistivity changes and the current flow through the sensor changes. The output from the Wheatstone bridge is a variable voltage output.

The first sensor 7 produces a variable voltage signal 9 which passes through a signal conditioner 10 and is routed to an analog-to-digital A/D converter 11. The second sensor 8 produces a signal 12 which passes through a signal conditioner 13 and is also routed to an A/D converter 11. A multiplexer or the like (not shown) can be used to handle multiple sensor signals 9, 12 with one A/D converter 11. Digital output from the A/D converter 11 is routed to a CPU 14. An electronic depth recorder 15 produces a digital depth recorder signal 16 which is also routed to the CPU 14.

The CPU 14 processes the sensor signals 9 and 12 and obtains their difference. Specifically, sensor signal 12 is subtracted from sensor signal 9 to produce a value representing a differential total-gas (DTG) signal. The depth recorder signal 16 is processed to calculate the rate of penetration (ROP) during drilling.

Additional information is processed by the CPU as necessary to calculate other parameters including mud fluid lag. Gas sensor output cannot be directly related to the actual position of the drilling bit due to the lag associated with the return of the mud from the bit to the gas trap and thus to the gas sensor. This information is plotted in a graphical format—depicted in the form of a chart 17 or on a computer screen.

The sensors 7, 8 are comprised of rare-earth, transition metal oxide sensors which are sintered and sandwiched between metallized surfaces or electrodes. It is known that the resistivity of the metal oxide to temperature is non-linear which makes the sensor ideal for temperature sensing applications. In this implementation, if current is applied, then the sensor is self-heating. If heat is constantly dissipated then the resistivity remains constant and the voltage across the metal oxide will be constant. Alternatively, if the surrounding environment causes the heat dissipation to vary (as it will if the quality or concentration of hydrocarbon changes) then the current or the voltage will vary.

Also, for the purposes of the present invention, these rare earth sensors are used for both the first and second sensors 7, 8. Sufficient variability exists between each commercially available thermistor sensor to enable selection of two having different responses when exposed to different gases.

The response of the first gas sensor 7 demonstrates a substantially consistent increase 18 in current for increasing concentrations of methane. For mixtures containing only methane and ethane (one can used natural gas also), the selected gas sensor 8 demonstrates a substantially consistent increase 19 in current for increasing concentrations of the gas mixture. For propane and butane mixtures (being heavier hydrocarbons) the same selected sensor 8 demonstrates a substantially consistent decrease 20 in current for increasing concentrations of the gas mixture. Simply, the second gas sensor responds in two ways on two different mixtures of gas.

Figure 3:
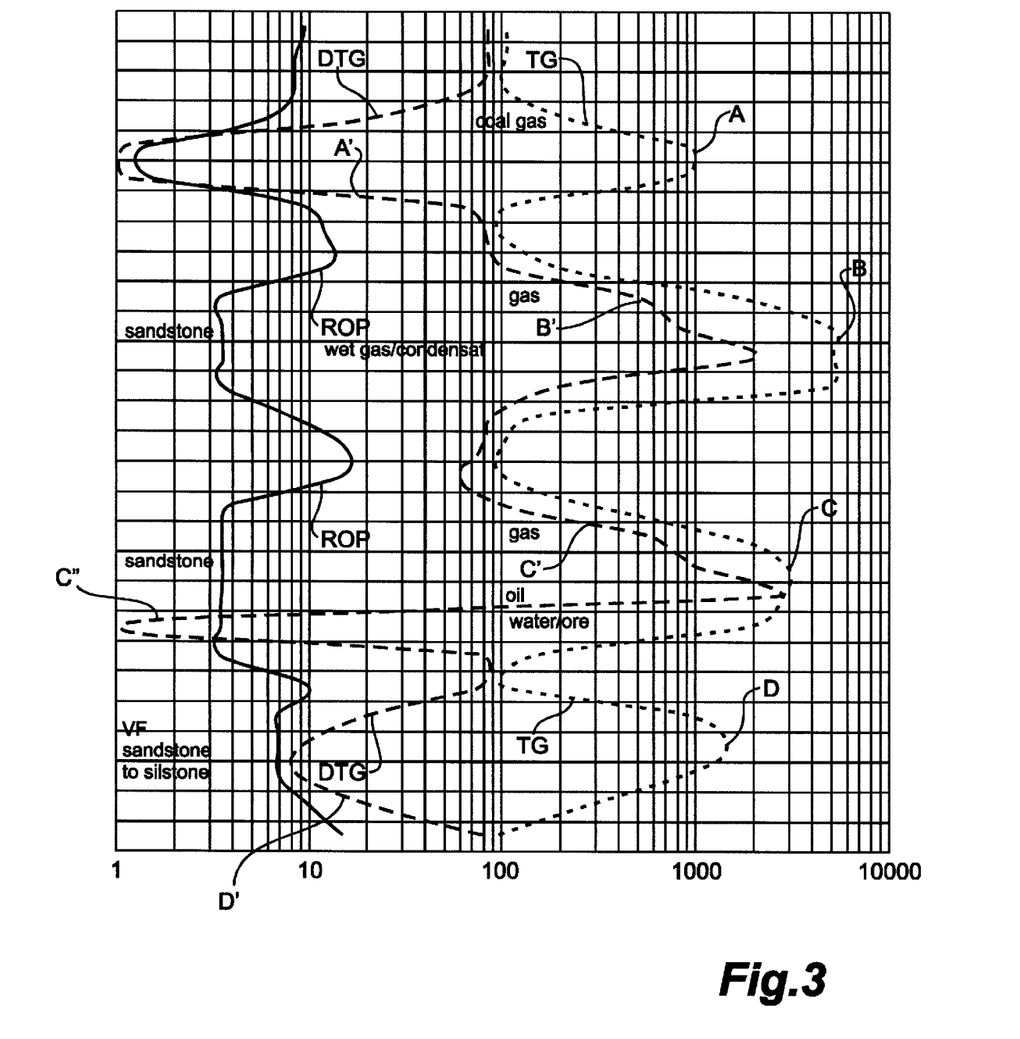
FIG. 3 is a chart trace illustrative of the output of the total-gas and differential total-gas sensors, the differential between the sensor signals and the rate of production for drilling through a sandstone formation.

When exposed to a mixture of gases, generally both sensors 7,8 respond with increasing current output 9,12 for the lighter hydrocarbons with a subtraction operation reducing the magnitude of the positive value of the resulting DTG output. For gases having high concentration of light hydrocarbons, signal 9 less signal 12 can result in a DTG output passing through zero or even becoming negative. An example is shown in FIG. 3 as negative peak A'.

However, as a gas mixture becomes heavier, the response of the DTG sensor 8 causes the current output 12 to drop significantly, with the subtraction operation resulting in an increased net DTG output. An example is shown in FIG. 3 as positive peak B'.

The numerical ratio of the values of the TG signal and the DTG signal is used as a simple means for establishing the relative concentration of heavy or light hydrocarbons in the extracted gas.

To summarize the TG and DTG functions, in a mixture of gases, the two detectors generally respond differently as the gas changes. The different response can be accentuated by obtaining the difference of the two signals. So, as drilling progresses through subterranean zones having different qualities of gases, these different qualities will be distinguished, whereas previously, one only knew quantity; that volatile hydrocarbons merely existed in determinable relative concentrations.

Having reference to FIG. 3, for example, if one drills through coal-methane/gas/then oil zones, the TG sensor 7 indicates there are either hydrocarbons or there are not. The DTG sensor 8 indicates whether or not the hydrocarbons are light or heavy. So, as shown, the TG registers hydrocarbons at each of three zones. The DTG does not register at all in the coal-methane. For coal methane, there are basically no heavy hydrocarbons. So one can eliminate that zone. Next, as one drills past the gas zone, the DTG indicates somewhat, but it won't be a very large response, as gas would be more in the C1 or C2 range and not in the heavy range. Lastly, when you pass the oil zone, the DTG response will be significant indicating there are heavy hydrocarbons there.

Figure 4:
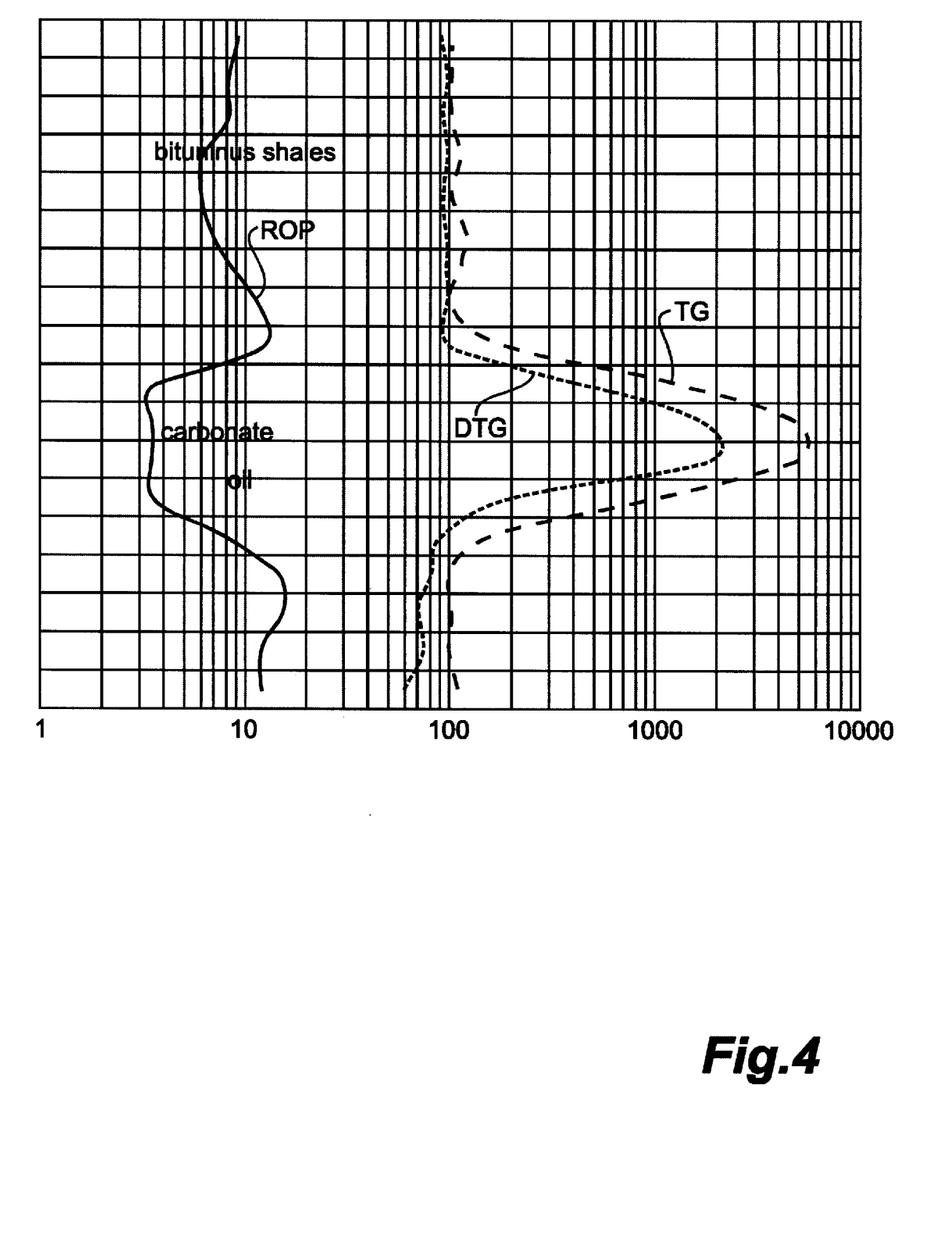
FIG. 4 is a chart trace illustrative of drilling through bituminous shales and carbonates.

As illustrated in FIG. 4, representing a well drilled in bituminous shales, note that both the TG and DTG curves became positive through a zone of carbonate oil, properly indicating not only the presence of hydrocarbons (prior art) but has been enhanced to demonstrate the presence of the heavier bituminous hydrocarbon components.

In summary, note that the TG indicates hydrocarbons at each of coal methane, hydrocarbon gas, and oil. The DTG output however yields variable analyses which suggest no oil results at coal methane, a small indication for the gas zone, and a much greater positive indication for the oil zone.

Hydrocarbon Ratio (HcR)

A ratio of TG/DTG (HcR) is indicative of the hydrocarbon ratio—a lower number being indicative of the presence of heavier hydrocarbons.

By combining the use of TG and DTG sensor analysis with drilling information, a hydrocarbon saturation index (HcSI) can be determined which is an indication of the fraction of hydrocarbons in the pores of a porous structure.

Whether Pores Contain Hydrocarbons

Just because a rock is porous is not instructive of whether the pore space contains hydrocarbons.

The hydrocarbon saturation index (HCSI) is illustrative of the relative fraction of hydrocarbon in the pore space of water or hydrocarbons. Clearly it is more preferable to have saleable hydrocarbons in the pore space rather than water.

Whether fluid in a pore is hydrocarbon is determined using parameters obtained or known while drilling including: Geometry—the volume of material removed by the bit, such as a 1 m gap knowing in diameter drill bit over time; Drillability—factors such as the lithology, drilling parameters like rate of penetration, force on the bit, bit rpm; and Hydrocarbon production and quality—measures of the volume of hydrocarbons released and their nature as measured by TG and DTG sensors from the gas trap, and the volume of hydrocarbons being measured in ppm and which is merely a diluted or fractional of the whole mud and thus evolved gas stream. This dilution factor is related to the total flow of mud which is determined by the rate of pumping or the pump stroke rate. The gas trap only pulls off a small slipstream of the evolved gases.

A computer program was developed for automatically processing streamed data from the rig (such as ROP, FOB and RPM) and streamed data from TG and DTG. Additional information, if not streamed, is input by an operator.

The nomenclature used throughout is as follows:

| Abbrev | Description | Default Value | Units |
| --- | --- | --- | --- |
| MW | Mud Weight | 1050 | kg/m³ |
| FOB | Force on Bit | 15 | MdN |
| RPM | revolutions per minute | 60 | 1/min |
| BS | Bit Size | 200 | mm |
| ROP | Rate of Penetration | | min/m |
| PS | mud pump stroke | 60 | stroke/min |
| PD | mud pump displacement | 0.020 | m3 |
| TO | Gas Trap Output (for TG and DTG) | 0.015 | m3 |
| CF | Compressibility Factor | 0.0005 | — |
| TG | Total Gas (1 unit = 100 ppm CH₄ equiv) | | units |
| DTG | Differential Total Gas (1 unit = 100 ppm CH₄ equiv) | | units |
| fPor | fDilut/NROP | | |
| fDilut | relationship between trap flow and mud flow | | |

Generally a computer program is used to store all the streamed data in a database and perform the following calculations. Numerical analysis permits an operator to perform many different types of calculations on the data based upon which variables are known and which the operator wishes to calculate.

The Process:

Prior to drilling of the well, certain variables are determined including BS, PD and PS. Further, while drilling the well, one records drilling data such as depth, ROP, FOB, RPM, MW all as a function of time.

Gases returning in the drilling mud are analysed using the gas trap and the TG and DTG sensors. The TG and DTG outputs are recorded as a function of time.

The trap output volumetric TO is known (it could also be a variable over time and would be streamed into the database also). The overall mud rate can be determined from the mud pump parameters PD and PS.

A mud lag calculation is performed to correlate the TG and DTG data with the actual depth and drilling data.

Drillability

A quantification of the drillability of the formation is determined with a first equation, relative to that at a FOB of 15 MdN, 60 rpm and 1000 kg/m$^3$:

$$factor = \frac{60*15*MW}{1000(FOB*RPM)} \quad (5)$$

Mud viscosity and mud filtrate (determined with standard filtration tests) can also be factored into the above equation.

Note that the mud weight (nominally 1000 kg/m$^3$) is also a factor when considering the Hydrocarbon Saturation Index. Mud weight affects whether it is easy or difficult to drill the formation. One of the characteristics of increasing mud weight is viscosity and another might be the buoyancy of the drill stem in heavy oil, which lightens the force on the bit.

Volume Factor

The Volume factor is the volume of the wellbore removed by the bit per unit meter of depth drilled. In other words, bit area*1 meter.

$$vfactor = \pi \left(0.001 \frac{BS}{2}\right)^2 \quad (2)$$

A Volume Drillability Factor is defined as $$\frac{factor}{vfactor}.$$

A normalised ROP is calculated by multiplying each ROP value over time by the Volume Drillabiltiy Factor.

$$NROP_i = ROP*\frac{factor}{vfactor} \quad (3)$$

An average normalised ROP is calculated over the formation of interest.

$$NROP_{avg} = \frac{\sum_{i=start}^{n} NROP_i}{n} \quad (8)$$

Dilution Factor for Gas Trap

The Dilution Factor between the gas trap slipstream flow and the overall flow of mud is:

$$fDilut = PD*PS*NROP_{avg}*\frac{PD*PS}{TO} \quad (9)$$

Porosity Factor is calculated as:

$$fPor_i = \frac{fDilut}{NROP_i} \quad (10)$$

Normalised Values

For Total Gas:

$$NTG_i = TG_i * fPor_i \quad (11)$$

For Differential Total Gas:

$$NDTG_i = DTG_i * fPor_i \quad (13)$$

Another factor is deemed the compression factor (CF). This is reflective of "Boyles Law" wherein pressure and volume are inversely related (P1V1=P2V2) and accordingly the volume of gas at the bottom of a wellbore is much smaller than the volume at the surface.

Accordingly, for the Hydrocarbon Saturation Index (HcSI):

$$HcSI_i = CF*NTG_i \quad (12)$$

Lastly, the Hydrocarbon Ratio HcR after the break is $$HcR_i = \frac{NTG_i}{NDTG_i} \quad (14)$$

When all these values are plotted on a log strip chart, the advantages of the quantification of the above parameters becomes clear.

EXAMPLES

Sample 1

Figure 5A:
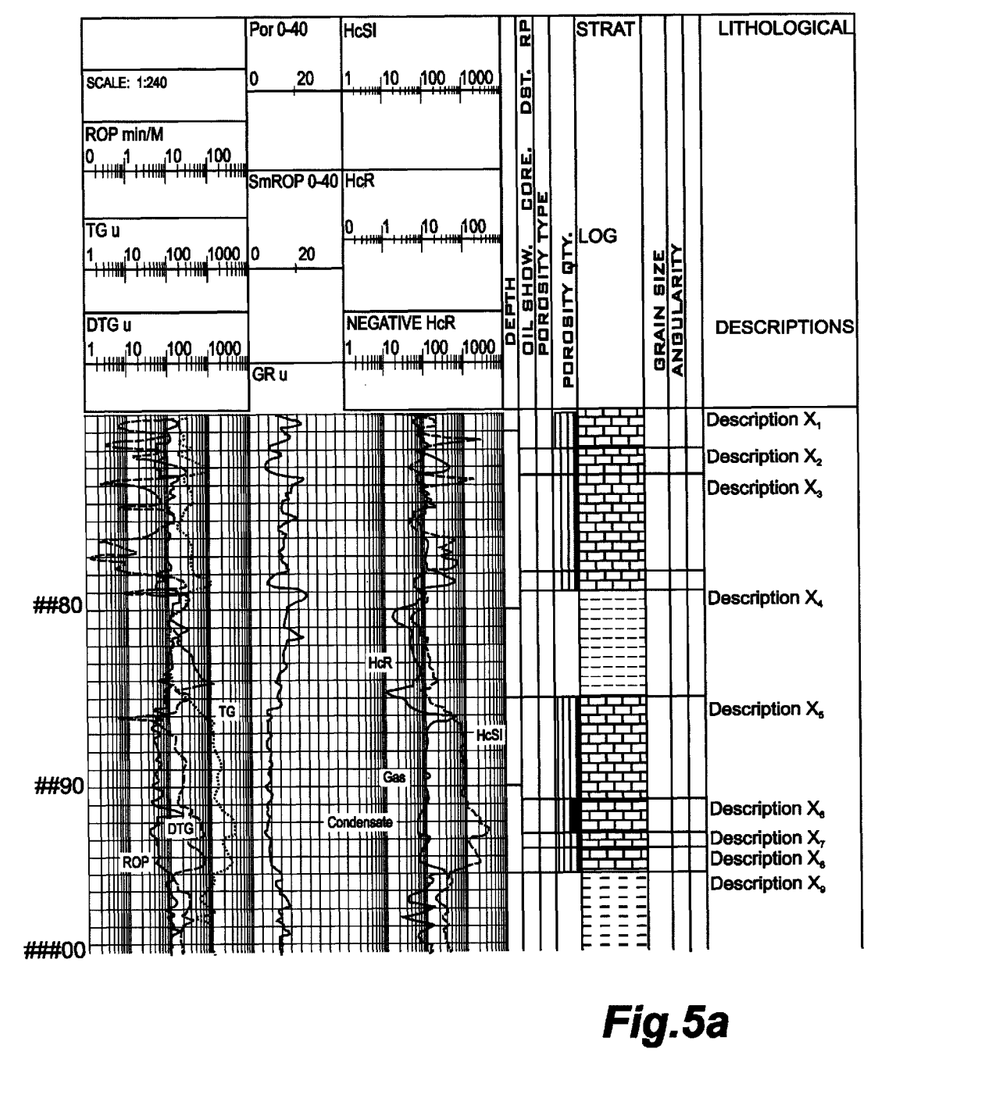
FIG. 5a is a log from a well illustrating the hydrocarbon saturation index and hydrocarbon ratio according to the first example.

FIG. 5a is a mud log from a first well. The depths have been altered for confidentiality. Only the 10's places are retained to identify depth, for instance, a depth of 3333 meters is referenced as ##33 m.

The traces are outputs from the computer program database and the values as defined and calculated above.

Accordingly, at a depth of ##93 meters, from left to right, the chart presents:

a. raw ROP b. raw DTG c. raw TG d. NROP e. HcR f. HcSI

In summary, while the conventional ROP and TG data identified ##85–##95 meters as being a zone of interest, use of DTG, HcR and HcSI narrowed the zone of interest to ##92–##95 or even more restricted to a 1 meter depth of ##92–##93.

More particularly, by inspecting the NROP (d), one can see a left shift at about ##85 m and a correcting right shift at about ##95 m. A left shift represents a faster ROP—or indication of a more porous formation. This is conventional so far and indicates a main zone of interest (Main Zone).

Note however the new and clearer indication of the Main Zone on the NROP trace (d) rather than the raw ROP trace (a).

Correspondingly, the TG trace (c) is elevated during this zone (85–95 m), indicative of hydrocarbons through the Main Zone. This TG trace is also conventional technology.

The novel DTG trace (b), shows a generally stable and low value between ##85 and ##91 m. Between ##91–##95, the DTG trace (b) makes two distinct upward spikes (s1 and s2) indicative of heavier hydrocarbons.

Further, HcSI values increased to a maximum of about 350 over a baseline of 8–10 or a ratio of 35–45 times. Experience has shown that HcSI of >7 times baseline are indicative of significant fractions of hydrocarbons in the pore.

The HcR trace (e) follows the DTG trace in reverse (understandably as it is a ratio of TG/DTG). At ##92.5 m, the HcR trace dropped to about 3, indicating heavier hydrocarbons, likely oil.

Empirically it is known that HcR value of <3 are oil, 5<HcR>8 being hydrocarbon Gas mixtures and HcR>10 are coal methane or non-hydrocarbon.

Figure 5B:
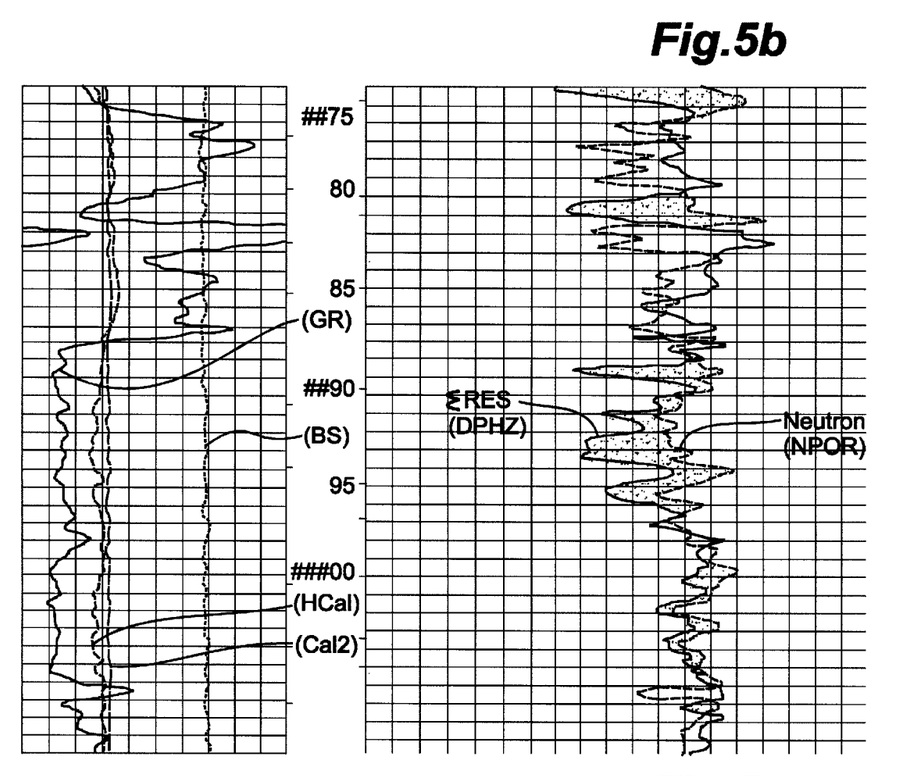
Figure 5C:
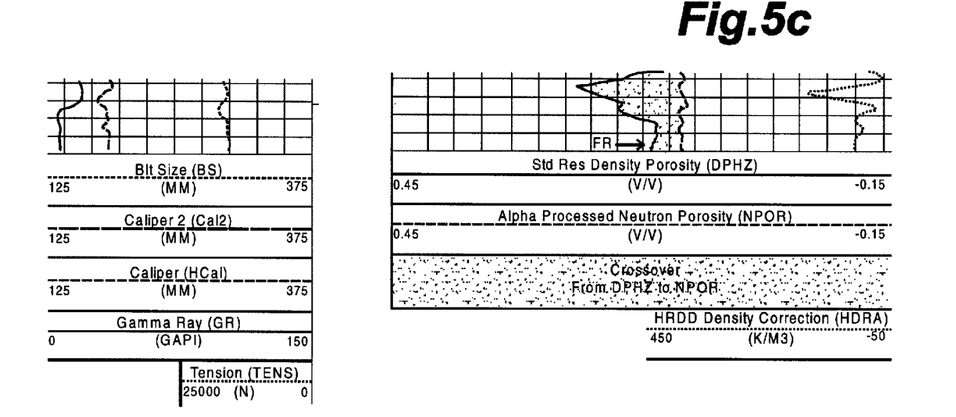
FIG. 5c is the second part of the E-log of FIG. 5b.

In FIG. 5b and continued on FIG. 5c, post-drilling E-logs provide support for the while-drilling analysis of the invention. The E-logs illustrate the Gamma Ray tool indicating Sandstone-like rather than Shale-like in the ##86–#105 m range. The neutron and resistivity Crossover are supportive of hydrocarbons, predominantly in the ##92–##96 m zone.

Sample 2

Figure 6:
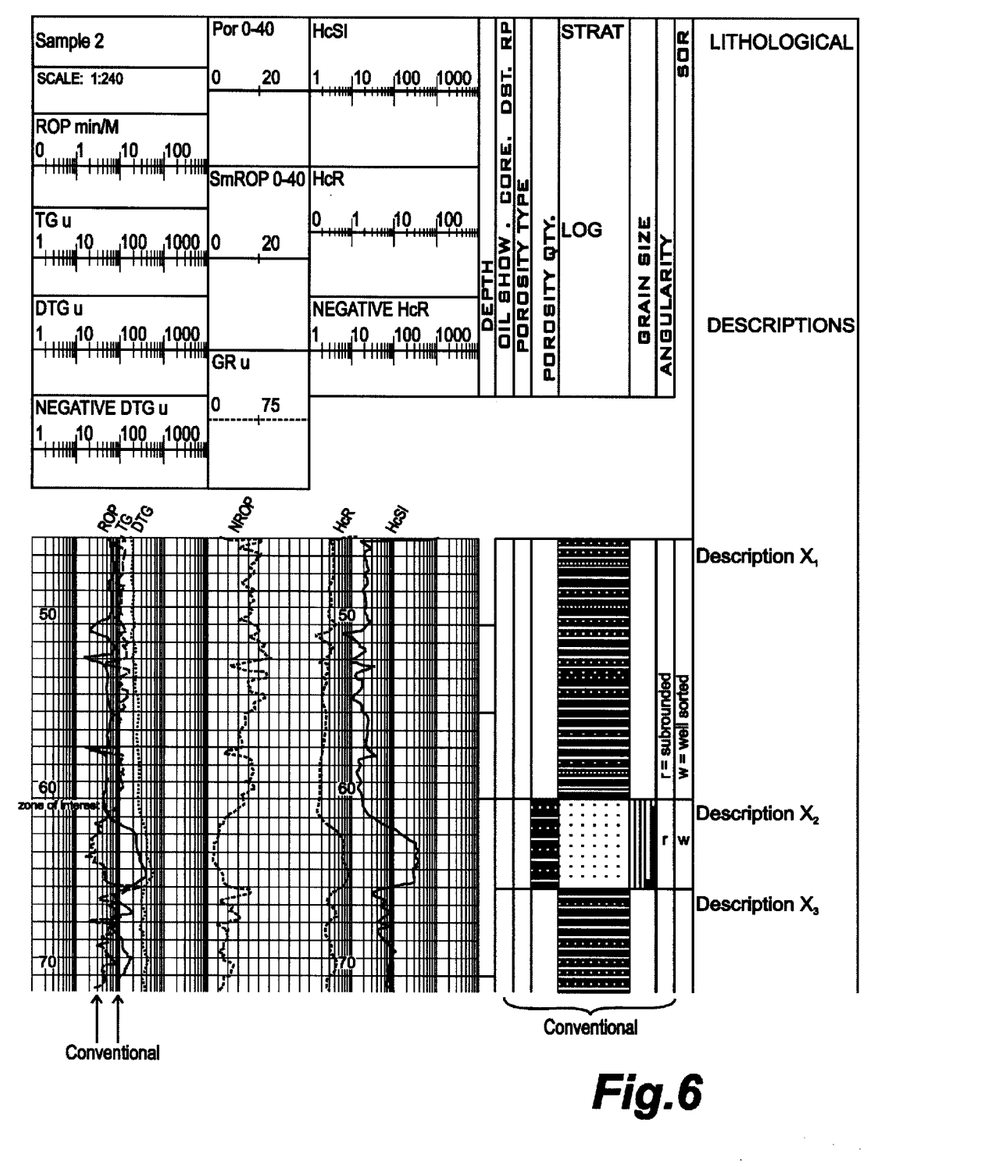
FIG. 6 is a log from a well illustrating the hydrocarbon saturation index and hydrocarbon ratio according to the second example.

FIG. 6 is a mud log from a second well. At a depth of ##63 meters, from left to right, the chart presents:

a. raw ROP b. raw TG c. raw DTG d. NROP e. HcR f. HcSI

Note that TG and DTG positions are inverse to those in Sample 1 above.

In summary, conventional ROP and TG data identified ##61–##66 meters as being a zone of interest. Use of DTG, HcR and HcSI corroborated the identified zone has added additional knowledge regarding the quality of the hydrocarbons. HcR values are consistently less than 1, indicative of oil.

HcSI values increased to a maximum of 300 over a baseline of 10 or a favourable ratio of about 30 times.

No E-logs were available.

Sample 3

Figure 7A:
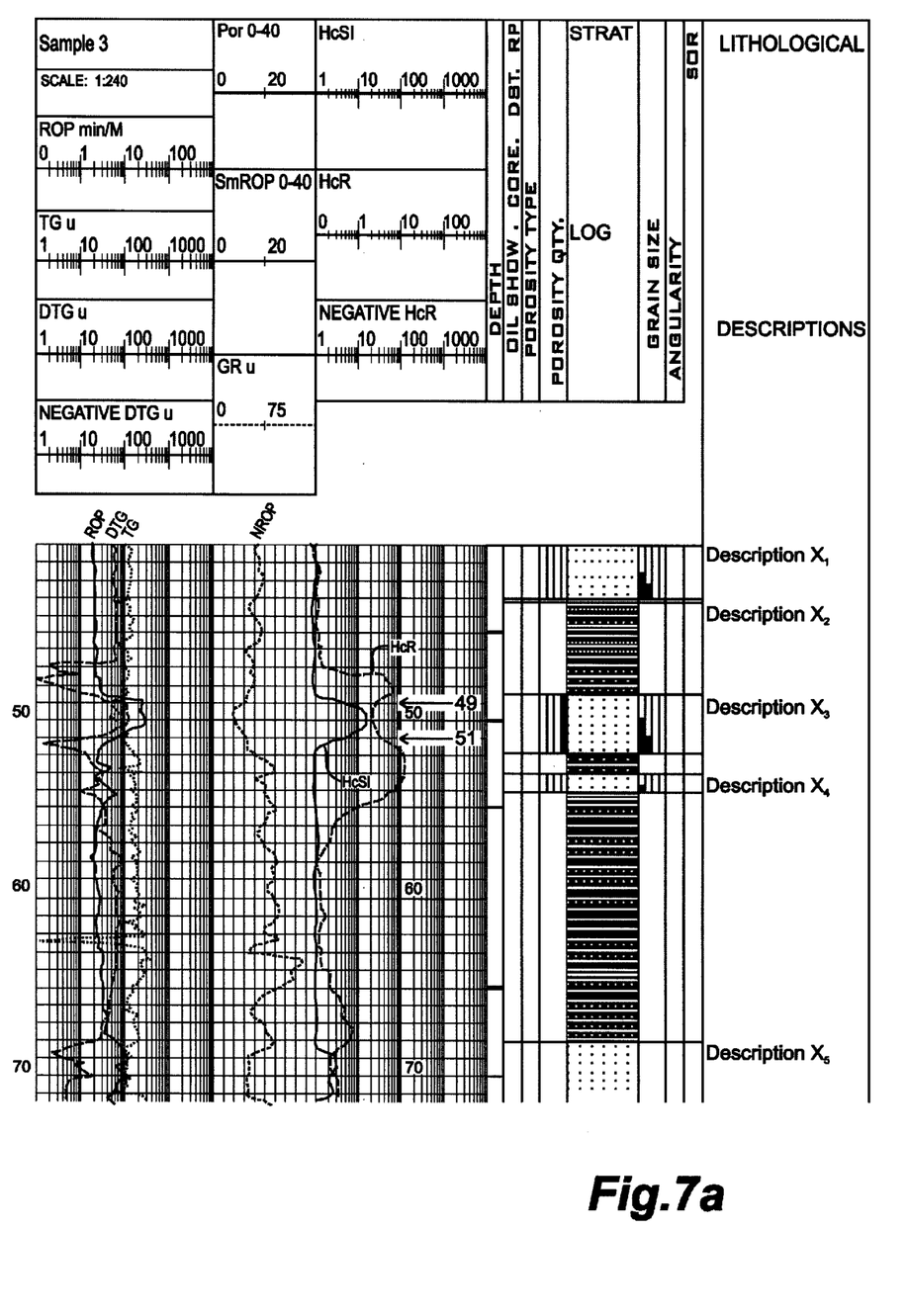
FIG. 7a is a log from a well illustrating the hydrocarbon saturation index and hydrocarbon ratio according to the third example.

FIG. 7a is a mud log from a third well. At a depth of ##50 meters, from left to right, the chart presents:

a. raw ROP b. raw DTG c. raw TG d. NROP e. HcSI f. HcR

In summary, conventional ROP and TG data identified ##49–##51 meters as being a zone of interest. The HcSI peak in the zone was about 10 times the baseline, indicating hydrocarbon. HcR dropped to about 2 showing that the hydrocarbons were heavy and indicative of oil.

Note that normalised ROP (NROP) more clearly displayed the break.

Figure 7B:
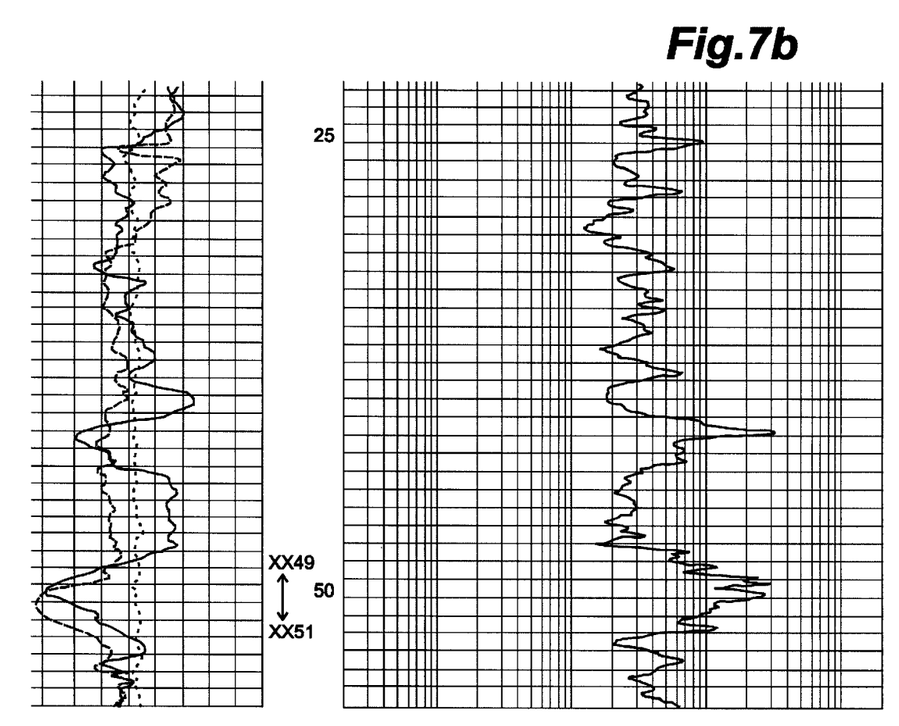
Figure 7C:
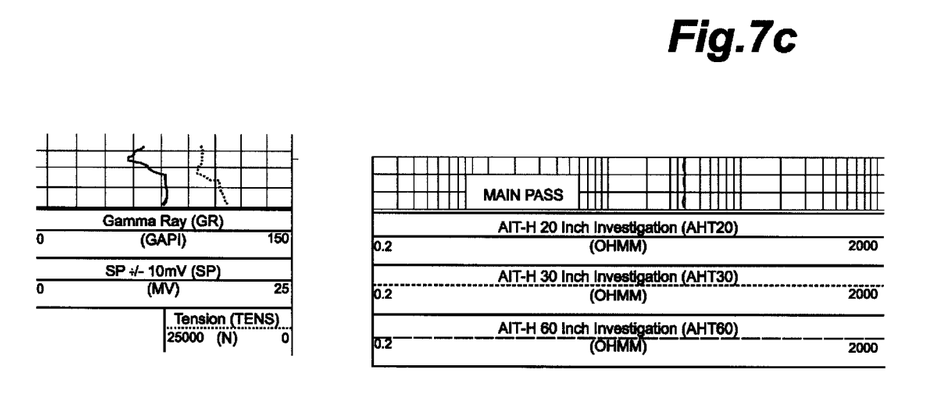
FIG. 7c is the second part of the E-log of FIG. 7b.

In FIG. 7b and continued on FIG. 7c, post-drilling E-logs provide support for the while-drilling analysis. The E-logs illustrate the Gamma Ray tool indicating a sharp localised drop for Sandstone-like rather than Shale-like in the ##49–##51 m range.

The embodiments of the invention in which an exclusive property or privilege is claimed are defined as follows:

1. A method for determining the characteristics of fluid in a fluid-containing formation while drilling, the formation of interest being traversed by a wellbore drilled by a drill bit, a volume of mud being circulated down through the bit and returning up the wellbore to the surface with gaseous traces of the formation fluid, comprising the steps of:

determining formation drillability characteristics including a rate of penetration (ROP);

normalizing the rate of penetration (NROP) to remove drillability characteristics which are other than those inherent in the formation;

determining an average NROP over the formation of interest;

analyzing a volume of the gaseous traces using a first gas sensor for establishing TG values which increase with increasing concentrations of hydrocarbons;

determining a dilution factor which is proportional to the average NROP and the circulated volume of mud and which is inversely proportional to the volume of gaseous traces analyzed by the TG sensor;

determining a porosity factor for the drilled formation which is proportional to the dilution factor and inversely proportional to the NROP;

normalizing the TG values by the porosity factor for establishing normalized TG values which are indicative of the fraction of the fluids which are hydrocarbons.

2. The method of claim 1 wherein the drillability characteristics comprise mud weight (MW), force on the drill bit (FOB) and drill bit rpm (RPM).

3. The method of claim 2 wherein normalization of the ROP comprises the steps of:

determining a drillability factor to ROP, the drillability factor being proportional to MW and inversely proportional to the product of FOB and RPM;

determining a volume factor to ROP, the volume factor being proportional to the area of the drill bit; and normalizing ROP as proportional to the drillability factor and inversely proportional to the volume factor.

4. The method of claim 3 wherein the normalization of the ROP comprises applying the following relationship:

$$NROP = ROP \cdot a \; constant \frac{\frac{MW}{FOB \cdot RPM}}{BS^2}$$

where BS is the bit diameter.

5. The method of claim 4 wherein the average ROP is determined by the following relationship:

$$NROP_{avg} = \frac{\sum_{i=start}^{n} NROP_i}{n}$$

where:

i is a discrete measure of ROP, and n is the number of discrete measures of ROP over the formation of interest.

6. The method of claim 3 further comprising applying a volume compressibility factor to the normalized TG.

7. The method of claim 1 wherein the quality of the fluid is determinable further comprising the steps of:

analyzing the volume of the gaseous traces using a second sensor for establishing values which decrease with increasing concentration of heavier hydrocarbons;

calculating differential total gas (DTG) values as the difference between the values from the first and second sensors, the DTG values increasing with increasing with increasing concentrations of heavier hydrocarbons;

normalizing the DTG values by the porosity factor for establishing normalized DTG values; and determining a ratio of normalized TG values over normalized DTG values for establishing hydrocarbon ratio values indicative of the quality of the hydrocarbons.

8. The method of claim 7 wherein the drillability characteristics comprise mud weight (MW), force on the drill bit (FOB) and drill bit rpm (RPM).

9. The method of claim 8 wherein normalization of the ROP comprises the steps of:

determining a drillability factor to ROP, the drillability factor being proportional to MW and inversely proportional to the product of FOB and RPM;

determining a volume factor to ROP, the volume factor being proportional to the area of the drill bit; and normalizing ROP as proportional to the drillability factor and inversely proportional to the volume factor.

10. The method of claim 9 wherein the normalization of the ROP comprises applying the following relationship:

$$NROP = ROP \cdot k \frac{\frac{MW}{FOB \cdot RPM}}{BS^2}$$

where BS is the bit diameter.

11. The method of claim 10 wherein the average ROP is determined by the following relationship:

$$NROP_{avg} = \frac{\sum_{i=start}^{n} NROP_i}{n}$$

where:
  i is a discrete measure of ROP, and
  n is the number of discrete measures of ROP over the formation of interest.

* * * * *